United States Patent
Watson et al.

[11] Patent Number: 6,152,915
[45] Date of Patent: Nov. 28, 2000

[54] DRAIN TUBE BELT AND SHOWER PACK KIT

[76] Inventors: Paul L. Watson; Viola M. Watson, both of 136 Lakeside Dr. East, Mossyrock, Wash. 98564

[21] Appl. No.: 09/274,854

[22] Filed: Mar. 23, 1999

[51] Int. Cl.⁷ .................................................. A61M 1/00
[52] U.S. Cl. ......................... 604/540; 604/343; 604/345; 604/353
[58] Field of Search .................................. 604/343, 345, 604/353, 351, 540

[56] References Cited

U.S. PATENT DOCUMENTS

| | | |
|---|---|---|
| D. 292,129 | 9/1987 | Aiello . |
| D. 311,453 | 10/1990 | Rice . |
| D. 335,759 | 5/1993 | Goude . |
| 4,087,864 | 5/1978 | La Bove et al. . |
| 5,142,702 | 9/1992 | Piloian . |
| 5,271,745 | 12/1993 | Fentress et al. . |
| 5,425,719 | 6/1995 | Lessing, Jr. . |
| 5,643,233 | 7/1997 | Turner ................................ 604/332 |
| 5,688,248 | 11/1997 | Lessing, Jr. . |
| 5,708,978 | 1/1998 | Johnsrud . |
| 5,853,396 | 12/1998 | Bennes et al. ....................... 604/179 |

*Primary Examiner*—Sharon Kennedy
*Assistant Examiner*—Kevin C. Sirmons
*Attorney, Agent, or Firm*—Thomas W. Secrest

[57] ABSTRACT

After an operation, a drain tube or drain tubes may be placed in the patient's body. Sometimes the drain tube is sutured into the open end of the body and hangs from the body. After a mastectomy, the drain tube is often sutured into the body of the patient. The drain tube hangs downwardly and there is a collection bulb on the end of the drain tube to the discomfort of the patient. The applicant has devised a strap which fits around the abdomen and on the strap there is a pocket for receiving the drain tube and the collection bulb. The patient can walk and maneuver with less discomfort because the pocket and the strap are bearing some of the weight of the drain tube and collection bulb and provide proper drainage. Also, there is disclosed a receptacle for holding the collection bulb by itself. The patient may want to take a shower or dress or undress. The collection bulb can be placed in this second receptacle. This allows freedom of movement of the hands and of the patient. The patient can position the receptacle on some of the plumbing features and accessory features in the shower as the receptacle does have a handle. Or, the patient can position the receptacle and the collection bulb on the rod holding the shower curtain. In essence, the patient can be made more comfortable with this invention as the patient has assistance in supporting the drain tube and the collection bulb.

9 Claims, 5 Drawing Sheets

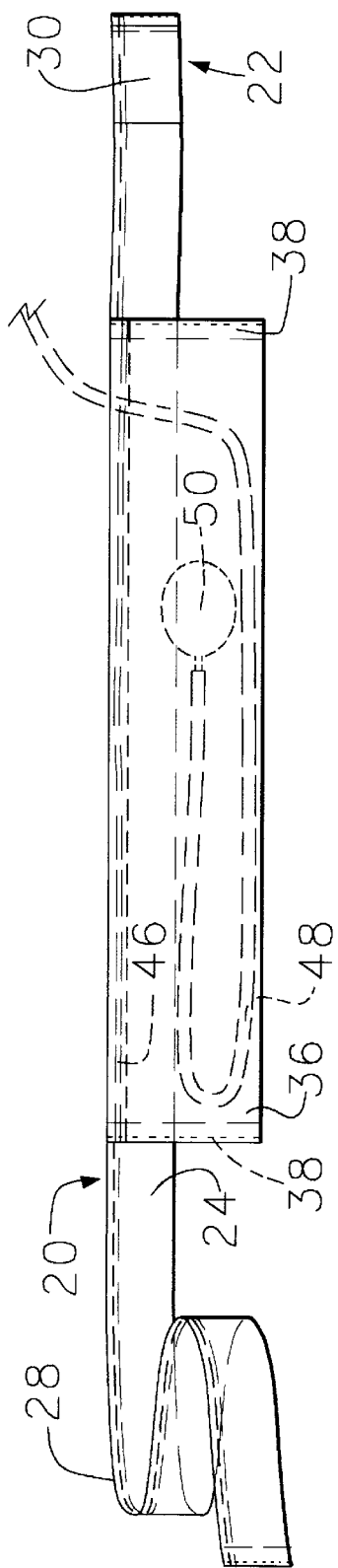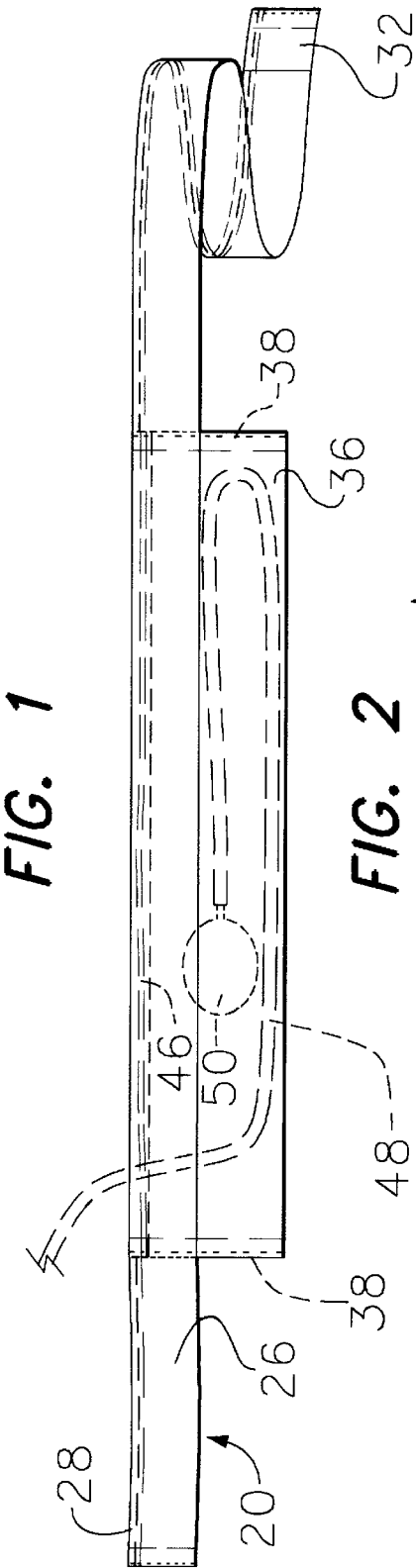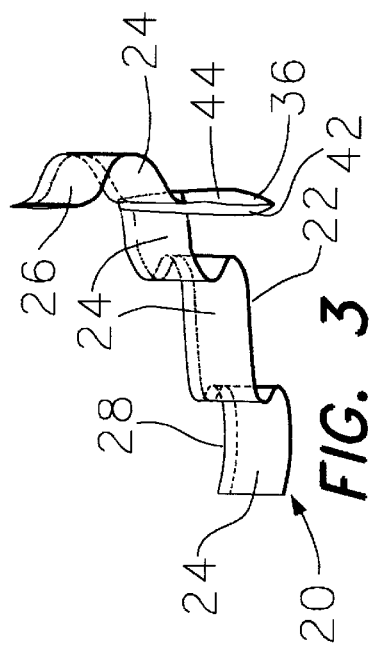

DRAIN TUBE BELT AND SHOWER PACK KIT

CROSS-REFERENCES TO RELATED PATENT APPLICATIONS (if any)

There is no related application.

STATEMENT AS TO RIGHTS TO INVENTIONS MADE UNDER FEDERALLY SPONSORED RESEARCH AND DEVELOPMENT (if any)

This invention and patent application was financed with private funds and there was no federal assistance in developing the invention and in the filing of the patent application.

REFERENCE TO A "MICROFICHE APPENDIX"

There is no microfiche appendix.

BACKGROUND OF THE INVENTION

1. Field of the Invention

The genesis of this invention is that one of the co-inventors had breast cancer. A mastectomy was performed. Two drain tubes were placed inside of her. These drain tubes extended from inside of her to outside of her. A drain tube is sutured into the body of the patient so that the drain tube cannot be accidentally removed. On the outer end of the drain tube there is positioned a collection bulb. The collection bulb may be at a lower internal pressure than the atmospheric pressure for the patient and the fluid from the patient's body flows into the collection bulb.

The tube and the collection bulb hang from the person's body. In the recovery period, the drain tube and the collection bulb become painful and also become a nuisance. A person walks or arises from a chair and the tube and collection bulb are swinging. Remember, the tube is sutured into the body of the patient. The weight of the tube and the collection bulb pull on the skin of the patient can cause pain and discomfort.

A first receptacle can be positioned around the patient's waist. The first receptacle can be a cloth such as cotton cloth. There is a pocket in the first receptacle and this pocket can receive the tube and the collection bulb. The first receptacle and the pocket support the tube and the collection bulb. This relieves some of the pain and discomfort of the tube being in the body of the individual and depending from the upper part of the body of the patient.

Another problem arises when the patient wants to take a shower. With the tube and collection bulb hanging from the patient, it is not practical to wear the first receptacle of cloth. The tube and the collection bulb hang from the patient and cause pain and discomfort. A partial solution is to have a second receptacle. The collection bulb is placed in the second receptacle. The second receptacle can be positioned on or hung from a plumbing feature in the shower or hung from a towel bar. The drain tube still hangs from the patient in the shower but the patient has freedom of movement with the hands for cleansing the body.

The second receptacle can be of a material that does not absorb and soak water. A suitable material may be a nylon mesh. The collection bulb can be placed in the second receptacle of nylon mesh and hung on the shower rail or a plumbing fixture. The material of the second receptacle may be hydrophobic so that it dries quickly. After the shower, the patient can put the first receptacle on the body. The tube and the collection bulb can be placed in the first receptacle to be supported by the first receptacle.

2. Description of the Related Art

There is a patent to Aiello, Des. Pat. No. 292,127, issue date of Sep. 29, 1987, for a "COMBINED I.V. CONTAINER HOLDING BAG AND STRAP". The subject invention differs from this patent in that the subject invention can hold the tube in a folded condition and also the collection bulb on the end of the tube. The receptacle of the subject invention is long so that the collection bulb and the tube can be placed in the first receptacle and when appropriate, the tube can be folded back on itself in a loose way so as not to restrict flow of drainage. This is not possible with Aiello. The holding bag of Aiello is not made of flexible cloth but is made of a rigid cloth structure.

There is a patent to James G. Rice, Des. Pat. No. 311,453, issue date of Oct. 23, 1990, which shows a "BODY ATTACHABLE BAG". The upper part of the body attachable bag appears to be stiff and of a thick material which cannot be folded and bent. The subject invention comprises a first receptacle of flexible cloth material which can be folded and bent upon itself.

There is patent to Charlotte Goude, Des. Pat. No. 335,759, issue date of May 25, 1993. Goude shows an "APRON". Goude does not show a receptacle for holding a drain tube with a collection bulb on the end of a drain tube.

There is a patent to LaBove et al, U.S. Pat. No. 4,087,864, issue date of May 9, 1978. LaBove et al teaches of a vest for fitting on and over the upper part of the patient's body. The subject invention is not for a vest and differs from the patent of Larry D. LaBove et al.

There is a patent to Gladys G. Piloian, U.S. Pat. No. 5,142,702, issue date of Sep. 1, 1992, for an "UPPER BODY OSTOMY GARMENT". This garment is, essentially, a vest as worn by a patient. The subject invention of a band or strap with a receptacle on the band or strap is not a vest and differs from Piloian.

SUMMARY OF THE INVENTION

In a mastectomy operation, after the breast has been removed, plastic tubes are placed beneath the skin of the breast and the pectoral muscle. These tubes are used to drain the fluid that will collect in the spaces created by the surgery and the removal of lymph glands. At the places where the tubes emerge, the tubes are sutured to the skin and attached to a small collection bulb in which there is a partial vacuum. The fluid flows from the body of the patient to the small collection bulb as the pressure in the small collection bulb is less than the pressure in the patient.

This invention is directed to relieving the patient of the weight of the tubes which have been surgically implanted in the body. Also, the weight of the collection bulb is removed. This invention also gives the patient the freedom to shower without having to hold the bulb in one hand during the shower. The first receptacle is for receiving the drain tube and the collection bulb on the end of the drain tube. The first receptacle is of cotton cloth, or equivalent, and can be folded and matted into a small unit when not being used. Then, the first receptacle can be positioned around the waist of the patient. The collection bulb and part of the tube are positioned in the first receptacle and supported in the first receptacle so as to lessen the tension on the tube sutured to the body of the patient.

There is a second receptacle for holding the collection bulb. In preparation to take a shower, the drain tube and the collection bulb can be separated from the first receptacle and placed in the second receptacle. The first receptacle can be removed from the patient's body. The second receptacle can be positioned on a plumbing fixture in the shower or on a rod for the shower curtain. This gives the patient freedom of movement in the shower and also relieves the patient of the weight of the collection bulb.

After the shower, the second receptacle can be removed from the plumbing fixture or the rod for the shower curtain and hung on a towel rack or wall hook to allow the patient to dry with both hands. Then the drain tube and the collection bulb can be placed in the dry first receptacle and worn by the patient.

OBJECTS AND ADVANTAGES

There are many objects and advantages of this invention.

One of these is to provide a support for a drain tube and a collection bulb for a person having a drain tube coming out of the body and which drain tube may be sutured into the body;

A further object is to provide the support for a drain tube so that the patient can, in comfort, walk and/or sit without the drain tube causing pain and discomfort;

An additional object and advantage is to provide a support for a drain tube without hindering the flow of body fluid through the drain tube and into the collection bulb at the end of the drain tube;

Another object is to provide a support for the collection bulb and which support can be positioned on a shower faucet or shower plumbing or a shower fixture so as to free the two hands of the patient taking a shower;

An additional object is to provide a support which allows the drain tube and collection bulb to be hidden from view and not seen by a visitor visiting the patient;

An additional object of the invention is to provide mastectomy patients and other patients with a very easy way to relieve the pain of weight of the collection bulb and provide way to shower and dry oneself with both hands free and nothing on the body preventing a thorough shower and no wet belt to have to wait to dry in addition to being a cosmetic factor in that the tube and the collection bulb are not visible;

Further, this invention allows the patient to remove the belt completely from oneself so as to shower and after showering to have a dry belt to put on as soon as the patient dries oneself;

The pocket going completely from side to side allows the tube to come from almost any site on the body; and Additional objects, advantages and novel features of the invention will be set forth in part in the description which follows, and in part will become apparent to those skilled in the art upon examination of the following or may be learned by the practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWING(S)

In the drawings, it is seen that:

FIG. 1 is a front elevation view of the integral pouch and attaching band with the attaching band in an expanded state;

FIG. 2 is a rear elevational view of the integral pouch and attaching band;

FIG. 3 is a perspective view showing part of the front of the attaching band and part of the rear of the attaching band and the end view of the pouch on the attaching band;

DETAILED DESCRIPTION OF THE INVENTION

Figure 4:
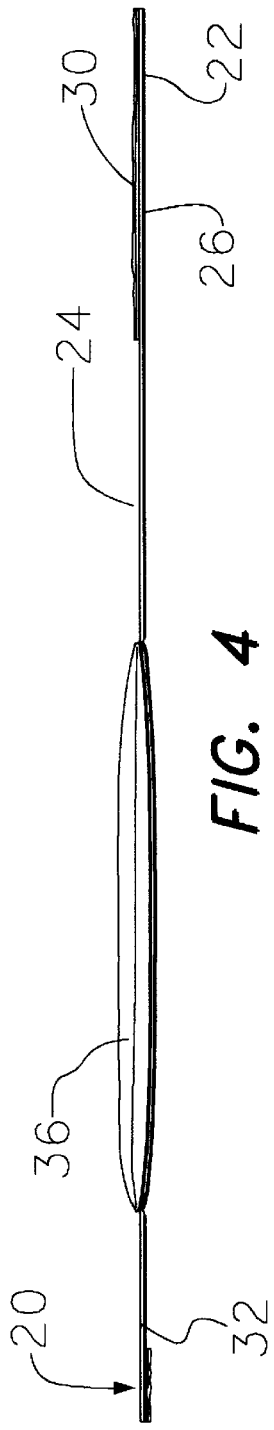
FIG. 4 is a bottom plan view of the integral pouch and attaching band.

With reference to FIGS. 1–11 it is seen that in FIG. 1 that there is a tube and bulb receptacle 20.

The receptacle 20 comprises a positioning band or handle 22 which is relatively long and of narrow width. The positioning band 22 has a front panel 24, see FIG. 1, and also a rear panel 26, see FIG. 2.

At the top of the band 22, there is stitching 28 to form the band.

In FIG. 1, it is seen that at the right end of the band 22 there is velcro 30 on the front panel 24.

In FIG. 2, it is seen that at the right end of the band 22 there is velcro 32 on the front of the rear panel 26.

Velcro comprises loops and catches. By pressing together the velcro members 30 and 32 there is formed a strong attachment between the two ends of the band 22.

As an alternative to the use of velcro 30 and 32 it is possible to use a safety pin.

In FIG. 1, it is seen that on the front of the panel 24 of the band 22 that there is a pouch 36. The pouch 36 comprises cloth which has been folded over on itself. The two outer ends, 38, are stitched together to form a pocket having closed ends and a closed bottom with an open top.

Figure 5:
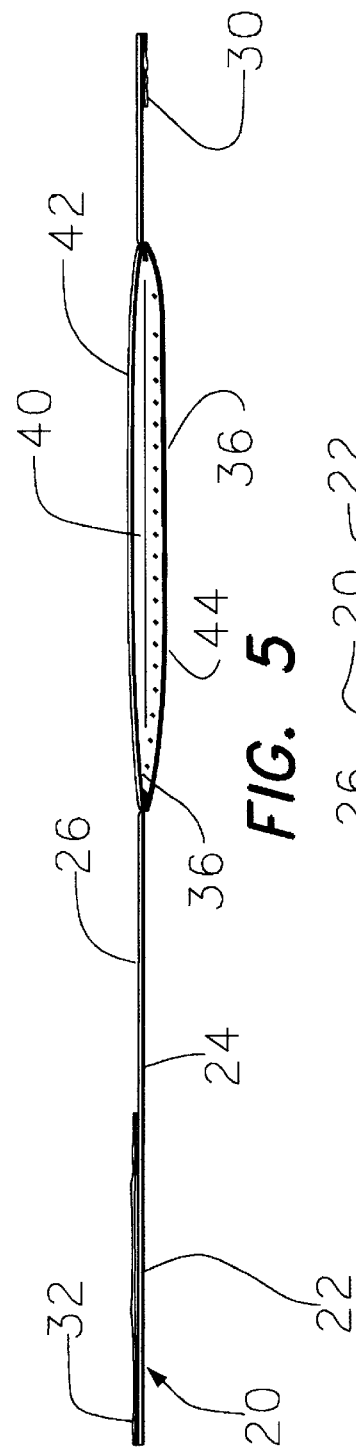
FIG. 5 is a top plan view of the integral pouch and attaching band and illustrating the pouch as being open for receiving an object.
Figure 6:
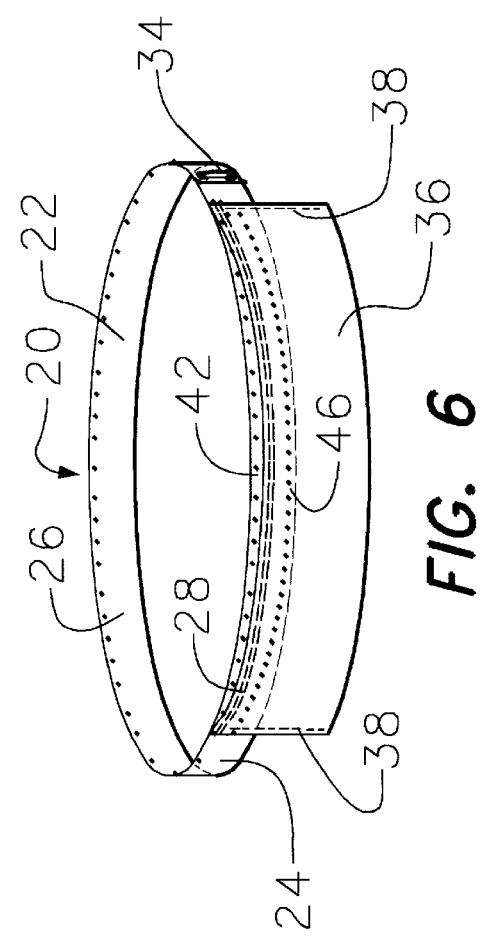
FIG. 6 is a perspective view looking at the integral pouch and attaching band and with the attaching band forming a loop and overly itself.
Figure 8:
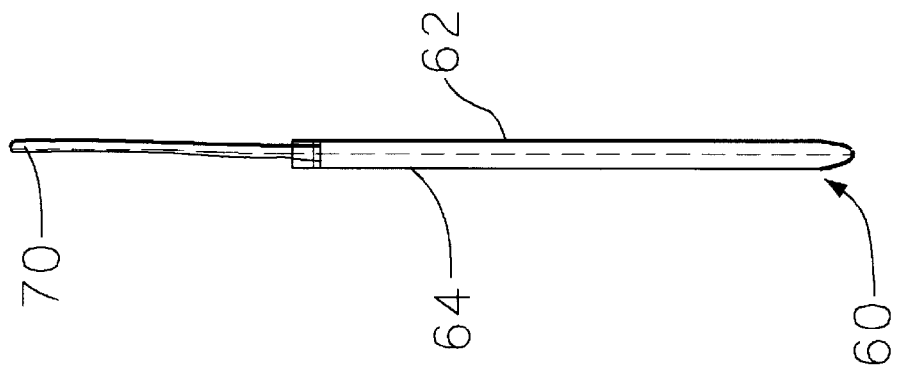
FIG. 8 is a side elevational view of the pouch and a handle and it is to be understood that the other side elevational view is the same.
Figure 7:
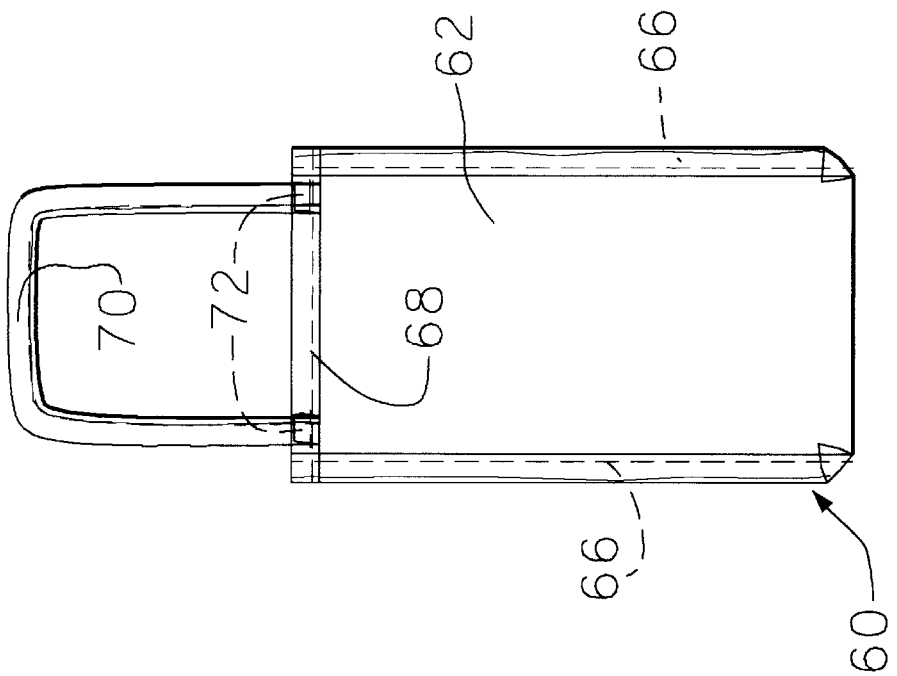
FIG. 7 is a front elevational view of the pouch and a handle connecting with the pouch and it is to be understood that the rear elevational view is the same as the front elevational view.
Figure 9:
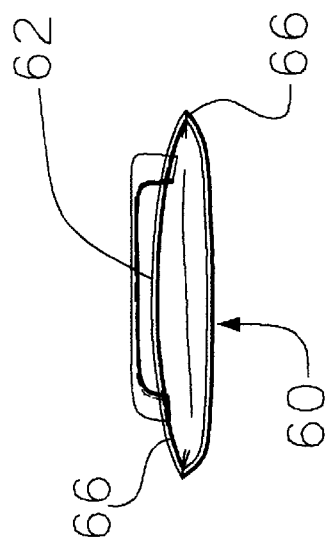
FIG. 9 is a bottom plan view of the pouch.

In FIG. 1, there is illustrated the tube in receptacle 20; the band 22; and the pouch 36. In FIG. 5, it is seen that the pouch has an open top 40. There is a rear panel 42 of the pouch 36 and a front panel 44 of the pouch 36. Also, there is stitching 46 connecting the rear panel 44 to the positioning band 22.

In FIGS. 1 and 2, it is seen that the outer end of drain tube 48 is in the pouch 36. On the free end of the drain tube 48, there is the collection bulb 50. The outer end of the drain tube 48 and the collection bulb 50 are supported in the pouch 36.

The reader is to understand that the pressure inside of the collection bulb 50 is less than the pressure inside the patient having the drain tube sutured to the body of the patient. This means that fluid will flow from inside of the patient and through the drain tube 48 to the collection bulb 50.

It is seen that the drain tube 48 and the collection bulb 50 are in the pouch 36 and are supported by the pouch 36. With respect to FIG. 6 it is seen that the band 22 overlaps itself and that the velcro members are pressed together so as to hold the band 22 in a circular shape around the abdomen of the patient. The circular band 22 will not slip down over the abdomen of the patient and therefore the pouch 36 acts as a support for the drain tube 48 and for the collection bulb 50. Part of the weight of the drain tube 48 and the collection bulb 50 are removed by having them positioned in the pouch 36. This makes it possible for the patient to move and walk. Actually, it makes it possible for the patient to move and walk without another party seeing the receptacle 20, the pouch 36, the drain tube 48, and the collection bulb 50. The patient will normally be wearing a dressing gown which will cover the band 22, the pouch 36, the drain tube 48, and the collection bulb 50.

FIG. 3 is a form of an end elevational view of the invention and illustrates the band 22, the pouch 36, the front panel 24, the rear panel 26, the top part of the band 22, and the stitching 28 at the top part of the band 22.

FIG. 4 is a bottom plan view of the invention and illustrates the band 22, the bottom of the pouch 36, the velcro 30, and the velcro 32.

FIG. 5 is a top plan view illustrating the receptacle 20, the top part of the band 22, the pouch 36 with the opening 40 for receiving the drain tube 48 and the receptacle 50; the velcro 32 and the velcro 30.

FIGS. 7–11 are directed to a receptacle for holding the collection bulb 50 while a person is taking a shower or dressing or undressing.

When a person is taking a shower it is a nuisance to have the collection bulb 50 dangling on the end of the drain tube 48.

The collection bulb 50 has some weight. Upon dangling from the end of a drain tube 48, the collection bulb 50 can swing back and forth and cause pain to the patient as the drain tube is sutured into the patient.

Also, when dressing and undressing the collection bulb 50 can move and cause some pain to the patient as the collection bulb 50 is on the end of the drain tube 48 and hangs downwardly on the drain tube 48.

The receptacle 60 may be made from, essentially, one piece of material such as a plastic nylon mesh. The receptacle 60 comprises a front panel 62, see FIG. 7 and 8. Also, a receptacle 60 comprises a rear panel 64, see FIGS. 8, 9, and 10.

The sides are folded back on themselves and stitched at 66, see FIGS. 7, 9, 10, and 11.

The top is folded back on itself and stitched at 68.

Figure 11:
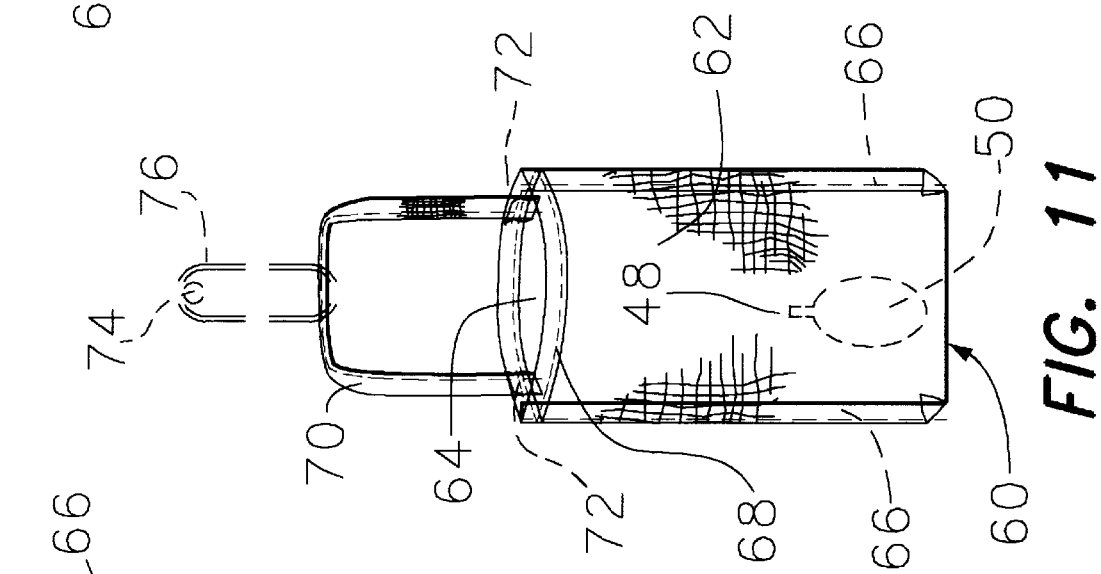
FIG. 11 is a front elevational view of the pouch and illustrates the opening in the top of the pouch; and, FIG. 12 is a fragmentary front elevational view of the torso of a person wearing the drain tube belt with the collection bulb in the pouch.
Figure 10:
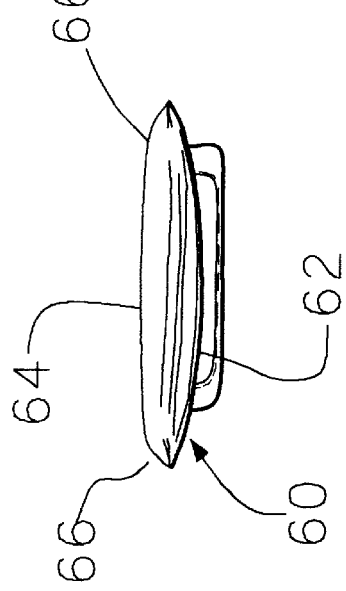
FIG. 10 is a top plan view of the pouch and the handle and illustrates the opening in the pouch.

The reader is to realize that the top of the front panel 62 and the top of the rear panel 64 are not stitched together but left free so as to form an opening, see FIGS. 10 and 11. The collection bulb 50 can be inserted through the opening defined by the upper part of the front panel 62 and the upper part of the rear panel 64 and held in the collection receptacle 60.

The material in construction of the front panel 62 and the rear panel 64 is a mesh. Preferably, the mesh is hydrophobic and is not attracted to water. There are certain materials which show these characteristics such as nylon, polyester, terephthalate, and silk. The mesh allows the water to drain freely away from the receptacle 60 and also since the mesh is hydrophobic there is no strong attraction between the mesh and the water.

The front panel 62 and the rear panel 64 are folded at the bottom so as to overly each other. The left side of the receptacle 60 is stitched so that the panel 62 and 64 are joined at the side.

The right side is stitched so that the panel 62 and 64 are joined together. The result is a receptacle 60 which is a pocket for receiving the collection bulb 50.

The bottom of 60 is closed while the upper part is open as the upper part of the front panel 62 and the upper part of the rear panel 64 can be spread apart for receiving the collection bulb 50.

Part of the mesh can be used to form a handle 70. One end of the handle 70 can be stitched to the upper part of the rear panel 64. The other end of the handle 70 can be stitched to the upper part of the rear panel 64.

The patient can hold onto the receptacle 60 by grasping onto the handle 70. The patient can hold onto the handle 70 and place the collection bulb 50 into the receptacle 60.

In a shower usually there is a horizontal bar holding a shower curtain. The horizontal bar or rod 74 can be used for attaching the receptacle 60 for holding the bulb 50 to an elevated position so that the patient can take a shower. The receptacle can also be hung on a faucet. There can be used a connector 76 for connecting with the handle 70 and also for connecting with the rod 74. In this manner, the collection bulb is not hanging from the patient but is in the receptacle 60. The receptacle 60 is being hung from the rod 74. The water can drip from the mesh in the receptacle 60. The mesh is not attracted to water so the water can readily drip away from the receptacle 60 so that the mesh can dry and be used again.

Figure 12:
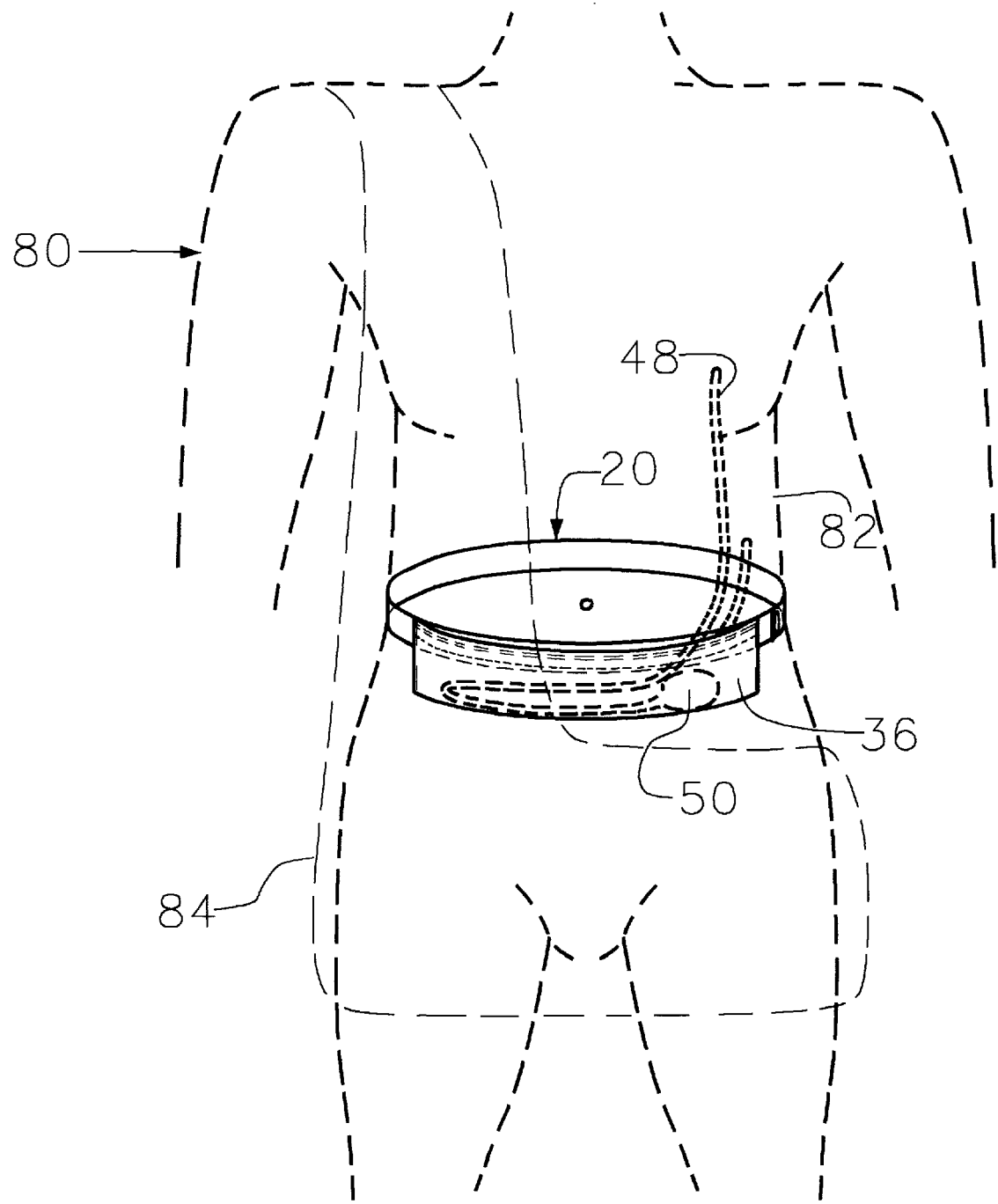

In FIG. 12 there is illustrated a fragmentary view of a person 80, in broken line, having a torso 82. There is a gown 84 partially removed to show the tube and bulb receptacle 20 around the waist of the of the person 80. A drain tube 48 is sutured into the chest area of the person 80. Part of the drain tube 48 is folded back on itself in the pouch 36 and connects with the collection bulb 50 in the pouch 36.

A receptacle for receiving and supporting medical apparatus attached to a person and said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; and a handle for holding and positioning said pocket, and operatively connecting with said pocket.

A receptacle for receiving and supporting medical apparatus attached to a person and said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; a handle for holding and positioning said pocket, and operatively connecting with said pocket; said pocket having a first pocket end and a second pocket. end; said handle comprising a band having a first band end extending beyond said first pocket end; said band having a second band end extending beyond said second pocket end; and said band being of sufficient length with the band wrapped around the torso of a person so that the first band end and the second band end overlap for positioning said receptacle on said person.

A receptacle for receiving and supporting medical apparatus attached to a person and said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; a handle for holding and positioning said pocket, and operatively connecting with said pocket; said pocket having a first pocket end and a second pocket end; said handle comprising a band having a first band end extending beyond said first pocket end; said band having a second band end extending beyond said second pocket end; said band being of sufficient length with the band wrapped around the torso of a person so that the first band end and the second band end overlap for positioning said receptacle on said person; and said pocket being relatively long and relatively shallow in depth so that the long part of said pocket is many times the depth of said pocket.

A receptacle for receiving and supporting medical apparatus attached to a person and said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; a handle for holding and positioning said pocket, and operatively connecting with said pocket; said pocket having a first pocket end and a second pocket end; said handle comprising a band having a first band end extending beyond said first pocket end; said band having a second band end extending beyond said second pocket end; said band being of sufficient length with the band wrapped around the torso of a person so that the first band end and the second band end overlap for positioning said receptacle on said person; said pocket being relatively long and relatively shallow in depth so that the long part of said pocket is many times the depth of said pocket; said front panel and said rear panel at said first pocket end being united; and said front panel and said rear panel at said second pocket end being united.

A receptacle for receiving and supporting medical apparatus attached to a person and said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; a handle for holding and positioning said pocket, and operatively connecting with said pocket; said pocket having a first pocket end and a second pocket: end; said handle comprising a band having a first band end extending beyond said first pocket end; said band having a second band end extending beyond said second pocket end; said band being of sufficient length with the band wrapped around the torso of a person so that the first band end and the second band end overlap for positioning said receptacle on said person; said pocket being relatively long and relatively shallow in depth so that the long part of said pocket is many times the depth of said pocket; said front panel and said rear panel at said first pocket end being united; said front panel and said rear panel at said second pocket end being united; and a connecting means for joining said first band end and said second band end.

A receptacle for receiving and supporting medical apparatus attached to a person and said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; a handle for holding and positioning said pocket, and operatively connecting with said pocket; said pocket having a first pocket end and a second pocket. end; said handle comprising a band having a first band end extending beyond said first pocket end; said band having a second band end extending beyond said second pocket end; said band being of sufficient length with the band wrapped around the torso of a person so that the first band end and the second band end overlap for positioning said receptacle on said person; said pocket being relatively long and relatively shallow in depth so that the long part of said pocket is many times the depth of said pocket; said front panel and said rear panel at said first pocket end being united; said front panel and said rear panel at said second pocket end being united; a connecting means for joining said first band end and said second band end; said connecting means comprising a first attaching means at said first band end and a second. attaching means at said second band end; and with said first attaching means and said second attaching means in contact said first band end and said second band end are joined forming a continuous band encircling the torso of said person.

A receptacle for receiving and supporting medical apparatus attached to a person and said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; a handle for holding and positioning said pocket, and operatively connecting with said pocket; said pocket having a first pocket end and a second pocket end; said handle comprising a band having a first band end extending beyond said first pocket end; said band having a second band end extending beyond said second pocket end; said band being of sufficient length with the band wrapped around the torso of a person so that the first band end and the second band end overlap for positioning said receptacle on said person; said pocket being relatively long and relatively shallow in depth so that the long part of said pocket is many times the depth of said pocket; said front panel and said rear panel at said first pocket end being united; said front panel and said rear panel at said second pocket end being united; a connecting means for joining said first band end and said second band end; said connecting means comprising a first attaching means at said first band end and a second attaching means at said second band end; with said first attaching means and said second attaching means in contact said first band end and said second band end are joined forming a continuous band encircling the torso of said person; and the long part of said pocket being attached to said band.

A receptacle for receiving and supporting medical apparatus attached to a person and said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; a handle for holding and positioning said pocket, and operatively connecting with said pocket; said handle having a first end and a second end; said first end operatively connecting with said pocket; and said second end operatively connecting with said pocket.

A receptacle for receiving and supporting medical apparatus attached to a person and said receptacle comprising a front panel and a rear panel defining a pocket; said pocket having a bottom and defining an opening between the upper part of said front panel and the upper part of said rear panel;

said opening allowing the ingress and egress of said medical apparatus into said pocket and out of said pocket; a handle for holding and positioning said pocket, and operatively connecting with said pocket; said handle having a first end and a second end; said first end operatively connecting with said pocket; said second end operatively connecting with said pocket; said pocket having a first pocket end and a second pocket end; said front panel and said rear panel at said first pocket end being united; and said front panel and said rear panel at said second pocket end being united.

A receptacle for receiving and supporting medical apparatus attached to a person and said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; a handle for holding and positioning said pocket, and operatively connecting with said pocket; said handle having a first end and a second end; said first end operatively connecting with said pocket; said second end operatively connecting with said pocket; said pocket having a first pocket end and a second pocket end; said front panel and said rear panel at said first pocket end being united; said front panel and said rear panel at said second pocket end being united; said receptacle having a plurality of openings to allow an aqueous medium to escape from the receptacle; and said receptacle being hydrophobic.

A combination of a receptacle and medical apparatus and comprising said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; a handle for holding and positioning said pocket, and operatively connecting with said pocket; and part of said medical apparatus being in said pocket.

A combination of a receptacle and medical apparatus and comprising said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; a handle for holding and positioning said pocket, and operatively connecting with said pocket; part of said medical apparatus being in said pocket; said medical apparatus comprising a drain tube and a fluid collection bulb; and said drain tube operatively connecting with said fluid collection bulb and with a patient for allowing fluid to drain from said patient to said collection bulb.

A combination of a receptacle and medical apparatus and comprising said receptacle comprising a front panel and a rear panel defining a pocket; said pocket having a bottom and defining an opening between the upper part of said front panel and the upper part of said rear panel; said opening allowing the ingress and egress of said medical apparatus: into said pocket and out of said pocket; a handle for holding and positioning said pocket, and operatively connecting with said pocket; part of said medical apparatus being in said pocket; said medical apparatus comprising a drain tube and a fluid collection bulb; said drain tube operatively connecting with said fluid collection bulb and with a patient for allowing fluid to drain from said patient to said collection bulb; said pocket having a first pocket end and a second pocket end; said handle comprising a band having a first band end extending beyond said first pocket end; said band having a second band end extending beyond said second pocket end; and said band being of sufficient length so that with the band wrapped around the torso of a person the first band end and the second band end overlap for positioning said receptacle on said person.

A combination of a receptacle and medical apparatus and comprising said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; a handle for holding and positioning said pocket, and operatively connecting with said pocket; part of said medical apparatus being in said pocket; said medical apparatus comprising a drain tube and a fluid collection bulb; said drain tube operatively connecting with said fluid collection bulb and with a patient for allowing fluid to drain from said patient to said collection bulb; said pocket having a first pocket end and a second pocket end; said handle comprising a band having a first band end extending beyond said first pocket end; said band having a second band end extending beyond said second pocket end; said band being of sufficient length so that with the band wrapped around the torso of a person the first band end and the second band end overlap for positioning said receptacle on said person; and said pocket being relatively long and relatively shallow in depth so that the long part of said pocket is many times the depth of said pocket.

A combination of a receptacle and medical apparatus and comprising said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; a handle for holding and positioning said pocket, and operatively connecting with said pocket; part of said medical apparatus being in said pocket; said medical apparatus comprising a drain tube and a fluid collection bulb; said drain tube operatively connecting with said fluid collection bulb and with a patient for allowing fluid to drain from said patient to said collection bulb; said pocket having a first pocket end and a second pocket end; said handle comprising a band having a first band end extending beyond said first pocket end; said band having a second band end extending beyond said second pocket end; said band being of sufficient length so that with the band wrapped around the torso of a person the first band end and the second band end overlap for positioning said receptacle on said person; said pocket being relatively long and relatively shallow in depth so that the long part of said pocket is many times the depth of said pocket; said front panel and said rear panel at said first pocket end being united; and said front panel and said rear panel at said second pocket end being united.

A combination of a receptacle and medical apparatus and comprising said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; a handle for holding and positioning said pocket, and operatively connecting with said pocket; part of said medical apparatus being in said pocket; said medical apparatus comprising a drain tube and a fluid collection bulb; said drain tube operatively connecting with said fluid collection bulb and with a patient for allowing fluid to drain from said patient to said collection bulb; said pocket having a first pocket end and a second pocket end; said handle comprising a band having a first band end extending beyond said first pocket end; said band having a second band end extending beyond said second pocket end; said band being of sufficient length so that with the band wrapped around the torso of a person the first band end and the second band end overlap for positioning said receptacle on said person; said pocket being relatively long and relatively shallow in depth so that the long part of said pocket is many times the depth of said pocket; said front panel and said rear panel at said first pocket end being united; said front panel and said rear panel at said second pocket end being united; and a connecting means for joining said first band end and said second band end.

A combination of a receptacle and medical apparatus and comprising said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; a handle for holding and positioning said pocket, and operatively connecting with said pocket; part of said medical apparatus being in said pocket; said medical apparatus comprising a drain tube and a fluid collection bulb; said drain tube operatively connecting with said fluid collection bulb and with a patient for allowing fluid to drain from said patient to said collection bulb; said pocket having a first pocket end and a second pocket end; said handle comprising a band having a first band end extending beyond said first pocket end; said band having a second band. end extending beyond said second pocket end; said band being of sufficient length so that with the band wrapped around the torso of a person the first band end and the second band end overlap for positioning said receptacle on said person; said pocket being relatively long and relatively shallow in depth so that the long part of said pocket is many times the depth of said pocket; said front panel and said rear panel at said first pocket end being united; said front panel and said rear panel at said second pocket end being united; a connecting means for joining said first band end and said second band end; said connecting means comprising a first attaching means at said first band end and a second attaching means at said second band end; and with said first attaching means and said second attaching means in contact said first band end and said second band end are joined to form a continuous band for encircling the torso of said person.

A combination of a receptacle and medical apparatus and comprising said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; a handle for holding and positioning said pocket, and operatively connecting with said pocket; part of said medical apparatus being in said pocket; said medical apparatus comprising a drain tube and a fluid collection bulb; said drain tube operatively connecting with said fluid collection bulb and with a patient for allowing fluid to drain from said patient to said collection bulb; said pocket having a first pocket end and a second pocket end; said handle comprising a band having a first band end extending beyond said first pocket end; said band having a second band end extending beyond said second pocket end; said band being of sufficient length so that with the band wrapped around the torso of a person the first band end and the second band end overlap for positioning said receptacle on said person; said pocket being relatively long and relatively shallow in depth so that the long part of said pocket is many times the depth of said pocket; said front panel and said rear panel at said first pocket end being united; said front panel and said rear panel at said second pocket end being united; a connecting means for joining said first band end and said second band end; said connecting means comprising a first attaching means at said first band end and a second attaching means at said second band end; with said first attaching means and said second attaching means in contact said first band end and said second band end are joined to form a continuous band for encircling the torso of said person; and the long part of said pocket being attached to said band.

A combination of a receptacle and medical apparatus and comprising said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; a handle for holding and positioning said pocket, and operatively connecting with said pocket; part of said medical apparatus being in said pocket; said handle having a first end and a second end; said first end operatively connecting with said pocket; said second end operatively connecting with said pocket; and said medical apparatus comprising a fluid collection bulb in said receptacle and supported by said receptacle.

A combination of a receptacle and medical apparatus and comprising said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; a handle for holding and positioning said pocket, and operatively connecting with said pocket; part of said medical apparatus being in said pocket; said handle having a first end and a second end; said first end operatively connecting with said pocket; said second end operatively connecting with said pocket; said medical apparatus comprising a fluid collection bulb in said receptacle and supported by said receptacle; said pocket having a first pocket end and a second pocket end; said front panel and said rear panel at said first pocket end being united; and said front panel and said rear panel at said second pocket end being united.

A combination of a receptacle and medical apparatus and comprising said receptacle comprising a front panel and a rear panel defining a pocket; said pocket having a bottom and defining an opening between the upper part of said front panel and the upper part of said rear panel; said opening allowing the ingress and egress of said medical apparatus into said pocket and out of said pocket; a handle for holding and positioning said pocket, and operatively connecting with said pocket; part of said medical apparatus being in said pocket; said handle having a first end and a second end; said first end operatively connecting with said pocket; said second end operatively connecting with said pocket; said medical apparatus comprising a fluid collection bulb in said receptacle and supported by said receptacle; said pocket having a first pocket end and a second pocket end; said front panel and said rear panel at said first pocket end being united; said front panel and said rear panel at said second pocket end being united; forming said receptacle to have a plurality of openings to allow an aqueous medium to escape from the receptacle; and selecting said receptacle to be hydrophobic.

A process for forming a receptacle for receiving and supporting medical apparatus, said process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; and operatively connecting a handle to said pocket for holding and positioning said pocket.

A process for forming a receptacle for receiving and supporting medical apparatus, said process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; and forming said band to be of sufficient length so that with the band wrapped around the torso of a person the first band end and the second band end overlap for positioning said receptacle on said person.

A process for forming a receptacle for receiving and supporting medical apparatus, said process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; and forming said pocket to be relatively long and relatively shallow in depth so that the long part of said pocket is many times the depth of said pocket.

A process for forming a receptacle for receiving and supporting medical apparatus, said process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; and uniting said front panel and said rear panel at said second pocket end.

A process for forming a receptacle for receiving and supporting medical apparatus, said process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; uniting said front panel and said rear panel at said second pocket end; and incorporating a connecting means for joining said first band and said second band.

A process for forming a receptacle for receiving and supporting medical apparatus, said process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; uniting said front panel and said rear panel at said second pocket end; incorporating a connecting means for joining said first band and said second band; said connecting means comprising a first attaching means on said first band and a second attaching means on said second band; and joining said first attaching means and said second attaching means to form a continuous and for encircling the torso of said person.

A process for forming a receptacle for receiving and supporting medical apparatus, said process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; uniting said front panel and said rear panel at said second pocket end; incorporating a connecting means for joining said first band and said second band; said connecting means comprising a first attaching means on said first band and a second attaching means on said second band; joining said first attaching means and said second attaching means to form a continuous and for encircling the torso of said person; and attaching the long part of said pocket to said band.

A process for forming a receptacle for receiving and supporting medical apparatus, said process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; uniting said front panel and said rear panel at said second pocket end; incorporating a connecting means for joining said first band and said second band; said connecting means comprising a first attaching means on said first band and a second attaching means on said second band; joining said first attaching means and said second attaching means to form a continuous and for encircling the torso of said person; attaching the long part of said pocket to said band; and forming said pocket of a pliable, flexible material which can be folded so that said material can overlap itself.

A process for forming a receptacle for receiving and supporting medical apparatus, said process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said handle to have a first end and a second end; operatively connecting said first end with said pocket; and operatively connecting said second end with said pocket.

A process for forming a receptacle for receiving and supporting medical apparatus, said process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said handle to have a first end and a second end; operatively connecting said first end with said pocket; operatively connecting said second end with said pocket; forming said pocket to have a first pocket end and a second pocket end; uniting said front panel and said rear panel at said first pocket end; and uniting said front panel and said rear panel at said second pocket end.

A process for forming a receptacle for receiving and supporting medical apparatus, said process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said handle to have a first end and a second end; operatively connecting said first end with said pocket; operatively connecting said second end with said pocket; forming said pocket to have a first pocket end and a second pocket end; uniting said front panel arid said rear panel at said first pocket end; uniting said front panel and said rear panel at said second pocket end; forming said receptacle to have a plurality of openings to allow an aqueous medium to escape from the receptacle; and selecting said receptacle to be hydrophobic.

A process for forming a combination of a receptacle for attaching to a person and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; and operatively connecting a handle to said pocket for holding and positioning said pocket.

A process for forming a combination of a receptacle for attaching to a person and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; and forming said band to be of sufficient length with the band wrapped around the torso of a person so that the first band end and the second band end overlap for positioning said receptacle on said person.

A process for forming a combination of a receptacle for attaching to a person and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length with the band wrapped around the torso of a person so that the first band end and the second band end overlap for positioning said receptacle on said person; and forming said pocket to be relatively long and relatively shallow in depth so that the long part of said pocket is many times the depth of said pocket.

A process for forming a combination of a receptacle for attaching to a person and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end pocket; forming said pocket to have a bottom and to define an opening between the upper part of said front panel and the upper part of said long and relatively shallow in depth so that the long part of said pocket is many times the depth of said pocket.

A process for forming a combination of a receptacle for attaching to a person and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length with the band wrapped around the torso of a person so that the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; and uniting said front panel and said rear panel at said second pocket end.

A process for forming a combination of a receptacle for attaching to a person and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length with the band wrapped around the torso of a person so that the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; uniting said front panel and said rear panel at said second pocket end; and incorporating a connecting means for joining said first band end and said second band end.

A process for forming a combination of a receptacle for attaching to a person and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length with the band wrapped around the torso of a person so that the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; uniting said front panel and said rear panel at said second pocket end; incorporating a connecting means for joining said first band end and said second band end; said connecting means comprising a first attaching means at said first band end and a second attaching means at said second band end; and joining said first attaching means and said second attaching means to form a continuous band for encircling the torso of said person.

A process for forming a combination of a receptacle for attaching to a person and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length with the band wrapped around the torso of a person so that the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; uniting said front panel and said rear panel at said second pocket end; incorporating a connecting means for joining said first band end and said second band end; said connecting means comprising a first attaching means at said first band end and a second attaching means at said second band end; joining said first attaching means and said second attaching means to form a continuous band for encircling the torso of said person; attaching the long part of said pocket to said band; forming said pocket of a pliable, flexible material which can be folded so that said material can overlap itself.

A process for forming a combination of a receptacle for attaching to a person and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said handle to have a first end and a second end; operatively connecting said first end with said pocket; and operatively connecting said second end with said pocket.

A process for forming a combination of a receptacle for attaching to a person and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said handle to have a first end and a second end; operatively connecting said first end with said pocket; operatively connecting said second end with said pocket; forming said pocket to have a first pocket end and a second pocket end; uniting said front panel and said rear panel at said first pocket end; and uniting said front panel and said rear panel at said second pocket end.

A process for forming a combination of a receptacle for attaching to a person and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said handle to have a first end and a second end; operatively connecting said first end with said pocket; operatively connecting said second end with said pocket; forming said pocket to have a first pocket end and a second pocket end; uniting said front panel and said rear panel at said first pocket end; uniting said front panel and said rear panel at said second pocket end; said pocket having a first pocket end and a second pocket end; and said front panel and said rear panel at said first pocket end being united.

A receptacle for receiving medical apparatus and made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; and operatively connecting a handle to said pocket for holding and positioning said pocket.

A receptacle for receiving medical apparatus and made by a process comprising forming a front panel and a rear panel to define a pocket; forming said pocket to have a bottom and to define an opening between the upper part of said front panel and the upper part of said rear panel to allow ingress and egress of said medical apparatus into said pocket: and out of said pocket; operatively connecting a handle to said pocket; for holding and positioning said pocket; forming said pocket to have a first pocket end and a second pocket end; forming said handle in the form of a band to have a first band end extending beyond said first pocket end; forming said handle to have a second band end extending beyond said second pocket end; and forming said band to be of sufficient length so that with the band wrapped around the torso of a person the first band end and the second band end overlap for positioning said receptacle on said person.

A receptacle for receiving medical apparatus and made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; and forming said pocket to be relatively long and relatively shallow in depth so that the long part of said pocket is many times the depth of said pocket.

A receptacle for receiving medical apparatus and made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; and uniting said front panel and said rear panel at said second pocket end.

A receptacle for receiving medical apparatus and made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; uniting said front panel and said rear panel at said second pocket end; incorporating a connecting means for joining said first band end and said second band end.

A receptacle for receiving medical apparatus and made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; uniting said front panel and said rear panel at said second pocket end; incorporating a connecting means for joining said first band end and said second band end; said connecting means comprising a first attaching means at said first band end and a second attaching means at said second band end; and joining said first attaching means and said second attaching means to form a continuous band for encircling the torso of said person.

A receptacle for receiving medical apparatus and made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; uniting said front panel and said rear panel at said second pocket end; incorporating a connecting means for joining said first band end and said second band end; said connecting means comprising a first attaching means at said first band end and a second attaching means at said second band end; joining said first attaching means and said second attaching means to form a continuous band for encircling the torso of said person; and attaching the long part of said pocket to said band.

A receptacle for receiving medical apparatus and made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; uniting said front panel and said rear panel at said second pocket end; incorporating a connecting means for joining said first band end and said second band end; said connecting means comprising a first attaching means at said first band end and a second attaching means at said second band end; joining said first attaching means and said second attaching means to form a continuous band for encircling the torso of said person; attaching the long part of said pocket to said band; and forming said pocket of a pliable, flexible material which can be folded so that said material can overlap itself.

A receptacle for receiving medical apparatus and made by a process; comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; uniting said front panel and said rear panel at said second pocket end; incorporating a connecting means for joining said first band end and said second band end; said connecting means comprising a first attaching means at said first band end and a second attaching means at said second band end; joining said first attaching means and said second attaching means to form a continuous band for encircling the torso of said person; attaching the long part of said pocket to said band; forming said pocket of a pliable, flexible material which can be folded so that said material can overlap itself; forming said handle to have a first end and a second end; operatively connecting said first end with said pocket; and operatively connecting said second end with said pocket.

A receptacle for receiving medical apparatus and made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; uniting said front panel and said rear panel at said second pocket end; incorporating a connecting means for joining said first band end and said second band end; said connecting means comprising a first attaching means at said first band end and a second attaching means at said second band end; joining said first attaching means and said second attaching means to form a continuous band for encircling the torso of said person; attaching the long part of said pocket to said band; forming said pocket of a pliable, flexible material which can be folded so that said material can overlap itself; forming said handle to have a first end and a second end; operatively connecting said first end with said pocket; operatively connecting said. second end with said pocket; forming said pocket to have a first pocket end and a second pocket end; uniting said front panel and said rear panel at said first pocket end; and uniting said front panel and said rear panel at said second pocket end.

A receptacle for receiving medical apparatus and made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; forming said pocket to be relatively long and relatively shallow in depth so that the long part of said pocket is man, times the depth of said pocket; uniting said front panel and said rear panel at said first pocket end; uniting said front panel and said rear panel at said second pocket end; incorporating a connecting means for joining said first band end and said second band end; said connecting means comprising a first attaching means at said first band end and a second attaching means at said second band end; joining said first attaching means and said second attaching means to form a continuous band for encircling the torso of said person; attaching the long part of said pocket to said band; forming said pocket of a pliable, flexible material which can be folded so that said material can overlap itself; forming said handle to have a first end and a second end; operatively connecting said first end with said pocket; operatively connecting said second end with said pocket; forming said pocket to have a first pocket, end and a second pocket end; uniting said front panel and said rear panel at said first pocket end; uniting said front panel and said rear panel at said second pocket end; said pocket having a first pocket end and a second pocket end; and said front panel and said rear panel at said first pocket end being united.

A combination of a receptacle and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; and operatively connecting a handle to said pocket for holding and positioning said pocket.

A combination of a receptacle and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; and forming said band to be of sufficient length so that with the band wrapped around the torso of a person the first band end and the second band end overlap for positioning said receptacle on said person.

A combination of a receptacle and medical apparatus wherein said receptacle receives and supports said medical apparatus, and said receptacle is made by a process comprising forming a front panel and a. rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; and forming said pocket to be relatively long and relatively shallow in depth so that the long part of said pocket is many times the depth of said pocket.

A combination of a receptacle and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; and uniting said front panel and said rear panel at said second pocket end.

A combination of a receptacle and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; uniting said front panel and said rear panel at said second pocket end; and incorporating a connecting means for joining said first band end and said second band end.

A combination of a receptacle and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; uniting said front panel and said rear panel at said second pocket end; incorporating a connecting means for joining said first band end and said second band end; said connecting means comprising a first attaching means at said first band end and a second attaching means at said second band end; and joining said first attaching means and said second attaching means to form a continuous band for encircling the torso of said person.

A combination of a receptacle and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; uniting said front panel and said rear panel at said second pocket end; incorporating a connecting means for joining said first band end and said second band end; said connecting means comprising a first attaching means at said first band end and a second attaching means at said second band end; joining said first attaching means and said second attaching means to form a continuous band for encircling the torso of said person; and attaching the long part of said pocket to said band.

A combination of a receptacle and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; forming said band to be of sufficient length so that with the band wrapped around the torso of a person the first band end and the second band end overlap for positioning said receptacle on said person; forming said pocket to be relatively long and relatively shallow in depth so that the long part of said pocket is many times the depth of said pocket; uniting said front panel and said rear panel at said first pocket end; uniting said front panel and said rear panel at said second pocket end; incorporating a connecting means for joining said first band end and said second band end; said connecting means comprising a first attaching means at said first band end and a second attaching means at said second band end; joining said first attaching means and said second attaching means to form a continuous band for encircling the torso of said person; attaching the long part of said pocket to said band; and forming said pocket of a pliable, flexible material which can be folded so that said material can overlap itself.

A combination of a receptacle and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; uniting said front panel and said rear panel at said first pocket end; and uniting said front panel and said rear panel at said second pocket end.

A combination of a receptacle and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; uniting said front panel and said rear panel at said first pocket end; uniting said front panel and said rear panel at said second pocket end; said pocket having a first pocket end and a second pocket end; and said front panel and said rear panel at said first pocket end being united.

A combination of a receptacle and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; uniting said front panel and said rear panel at said first. pocket end; uniting said front panel and said rear panel at said second pocket end; said pocket having a first pocket end and a second pocket end; said front panel and said rear panel at said first pocket end being united; positioning a first receptacle on the person; and positioning the outer part of said drainage tube in said first receptacle with said first receptacle supporting said drainage tube.

A combination of a receptacle and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; uniting said front panel and said rear panel at said first pocket end; uniting said front panel and said rear panel at said second pocket end; said pocket having a first pocket end and a second pocket end; said front panel and said rear panel at said first pocket end being united; positioning a first receptacle on the person; positioning the outer part of said drainage tube in said first receptacle with said first receptacle supporting said drainage tube; connecting a collections bulb with the outer part of the drainage tube; and positioning the outer part of said drainage tube and said collection bulb in said first receptacle with said first receptacle supporting said drainage tube and said collection bulb.

A combination of a receptacle and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; uniting said front panel and said rear panel at said first pocket end; uniting said front panel and said rear panel at said second pocket end; said pocket having a first pocket end and a second pocket end; said front panel and said rear panel at said first pocket end being united; positioning a first receptacle on the person; positioning the outer part of said drainage tube in said first receptacle with said first receptacle supporting said drainage tube; connecting a collection bulb with the outer part of the drainage tube; positioning the outer part of said drainage tube and said collection bulb in said first receptacle with said first receptacle supporting said drainage tube and said collection bulb; forming said first receptacle to have a front panel and a rear panel defining a pocket; forming said pocket to have a bottom and to define an opening between the upper part of said front panel and the upper part of said rear panel to allow ingress and egress of said drainage tube and said collection bulb into said pocket and out of said pocket; and operatively connecting a handle to said pocket for holding and positioning said pocket.

A combination of a receptacle and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; uniting said front panel and said rear panel at said first pocket end; uniting said front panel and said rear panel at said second pocket end; said pocket having a first pocket end and a second pocket end; said front panel and said rear panel at said first pocket end being united; positioning a first receptacle on the person; positioning the outer part of said drainage tube in said first receptacle with said first receptacle supporting said drainage tube; connecting a collection bulb with the outer part of the drainage tube; positioning the outer part of said drainage tube and said collection bulb in said first receptacle with said first receptacle supporting said drainage tube and said collection bulb; forming said first receptacle to have a front panel and a rear panel defining a pocket; forming said pocket to have a bottom and to define an opening between the upper part of said front panel and the upper part of said rear panel to allow ingress and egress of said drainage tube and said collection bulb into said pocket and out of said pocket; operatively connecting a handle to said pocket for holding and positioning said pocket; forming said pocket to have a first pocket end and a second pocket end; forming said handle in the form of a band to have a first band end extending beyond said first pocket end; forming said handle to have a second band end extending beyond said second pocket end; and forming said band to be of sufficient length with the band wrapped around the torso of a person, the first band end and the second band end overlap for positioning said receptacle on said person.

A combination of a receptacle and medical apparatus wherein said receptacle receives and supports said medical apparatus, and said receptacle is made by a process comprising forming a front panel and a rear panel to define a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; forming said pocket to have a first pocket end and a second pocket end; uniting said front panel and said rear panel at said first pocket end; uniting said front panel and said rear panel at said second pocket end; said pocket having a first pocket end and a second pocket end; said front panel and said rear panel at said first pocket end being united; positioning a first receptacle on the person; positioning the outer part of said drainage tube in said first receptacle with said first receptacle supporting said drainage tube; connecting a collection bulb with the outer part of the drainage tube; positioning the outer part of said drainage tube and said collection bulb in said first receptacle with said first receptacle supporting said drainage tube and said collection bulb; forming said first receptacle to have a front panel and a rear panel defining a pocket; forming said pocket to have a bottom and to define an opening between the upper part of said front panel and the upper part of said rear panel to allow ingress and egress of said drainage tube and said collection bulb into said pocket and out of said pocket; operatively connecting a handle to said pocket for holding and positioning said pocket; forming said pocket to have a first pocket end and a second pocket end; forming said handle in the form of: a band to have a first band end extending beyond said first pocket end; forming said handle to have a second band end extending beyond said second pocket end; forming said band to be of sufficient length with the band wrapped around the torso of a person, the first band end and the second band end overlap for positioning said receptacle on said person; forming said pocket of a pliable, flexible material which can be folded so that said material can overlap itself.

A process for making more comfortable a person having a drainage tube both inside of the person and outside of the person and with a collection bulb connecting, on the outside of the person, with the drainage tube, said process comprising forming a front panel and a rear panel defining a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; separating and placing said collection bulb in said receptacle; a support near the person; and positioning the receptacle containing said collection bulb on said support external to the person.

A process for making more comfortable a person having a drainage tube both inside of the person and outside of the person and with a collection bulb connecting, on the outside of the person, with the drainage tube, said process comprising forming a front panel and a rear panel defining a pocket; forming said pocket to have a bottom and to define an opening between the upper part of said front panel and the upper part of said rear panel to allow ingress and egress of said medical apparatus into said pocket and out of said pocket; operatively connecting a handle to said pocket for holding and positioning said pocket; separating said collection bulb and said drainage tube and placing said collection bulb in said receptacle; a support near the person; positioning the receptacle containing said collection bulb on said support external to the person; forming said pocket to have a first pocket end and a second pocket end; uniting said front panel and said rear panel at said first pocket end; and uniting said front panel and said rear panel at said second pocket end.

A process for making a person more comfortable in taking a shower said person having a drainage tube both inside of the person and outside of the person and a collection bulb connecting, on the outside of the person, with the drainage tube; said process comprising forming a receptacle, for receiving and supporting said collection bulb, to have a front panel and a rear panel defining a pocket; forming an opening between the upper part of said front panel and the upper part of said rear panel; said opening allowing the ingress and egress of said collection bulb into said pocket and out of said pocket; forming a handle for holding and positioning said pocket, and operatively connecting with said pocket; said handle having a first end and a second end; positioning said collection bulb in the pocket in said receptacle; a support external to the person; and positioning said receptacle and said bulb on said support external to said person to allow freedom of movement by the person taking the shower.

What is claimed is:

1. A receptacle for receiving and supporting medical apparatus attached to a person and said receptacle comprising:
   a. a unitary one piece pouch comprising a front pouch panel and a rear pouch panel and having a first pouch end and a second pouch end;
   b. said front pouch panel and said rear pouch panel joining at said first pouch end;
   c. said front pouch panel and said rear pouch panel joining at said second pouch end;
   d. the upper part of said front pouch panel and the upper part of said rear pouch panel being separate and defining an opening;
   e. said unitary one piece pouch defining a bottom;
   f. said opening allowing the ingress and egress of said medical apparatus into said pouch and out of said pouch;
   g. a handle for holding and positioning said pouch, and operatively connecting with said pouch;
   h. said handle comprising a band having a first band end extending beyond said first pouch end;
   i. said band having a second band end extending beyond said second pocket end;
   j. said band being of sufficient length with the band wrapped around the torso of a person so that the first band end and the second band end overlap for positioning said receptacle on said person;
   k. said pouch being relatively long and relatively shallow in depth so that the long part of said pouch is many times the depth of said pouch;
   l. a connecting means for joining said first band end and said second band end;
   m. said connecting means comprising a first attaching means at said first band end and a second attaching means at said second band end;
   n. with said first attaching means and said second attaching means; in contact said first band end and said second band end are joined forming a continuous band encircling the torso of said person;
   o. the long upper part of said rear pouch panel joining the front panel of said band to define a horizontal opening in said pouch for receiving said medical apparatus; and
   p. said pouch being of a pliable, flexible material which can be folded so that said material can overlap itself.

2. A receptacle for receiving and supporting medical apparatus attached to a person and said receptacle comprising:
   a. a unitary one piece pouch comprising a front pouch panel and a rear pouch panel and having a first pouch end and a second pouch end;

b. said front pouch panel and said rear pouch panel joining at said first pouch end;

c. said front pouch panel and said rear pouch panel joining at said second pouch end;

d. the upper part of said front pouch panel folding back on itself and joining itself;

e. the upper part of said rear pouch panel folding back on itself and joining itself;

f. the upper part of said front pouch panel and the upper part of said rear pouch panel being separate and defining an opening;

g. said unitary one piece pouch defining a bottom;

h. said opening allowing the ingress and egress of said medical apparatus into said pouch and out of said pouch;

i. a handle for holding and positioning said pouch, and operatively connecting with said pouch;

j. said pouch being relatively short in length and relatively deep in depth so that the deep part is greater than said length;

k. said handle having a first end and a second end;

l. said first end operatively connecting with said pouch;

m. said first end connecting with the upper part of said pouch rear panel;

n. said second end connecting with the upper part of said pouch rear panel;

o. said first end and said second end being spaced apart;

p. said receptacle having a plurality of openings to allow an aqueous medium to escape from the receptacle; and q. said receptacle being hydrophobic.

3. A combination of a receptacle and medical apparatus comprising:

a. a unitary one piece pouch comprising a front pouch panel and a rear pouch panel and having a first pouch end and a second pouch end;

b. said front pouch panel and said rear pouch panel joining at said first pouch end;

c. said front pouch panel and said rear pouch panel joining at said second pouch end;

d. the upper part of said front pouch panel and the upper part of said rear pouch panel being separate and defining an opening;

e. said unitary one piece pouch defining a bottom;

f. said opening allowing the ingress and egress of said medical apparatus into said pouch and out of said pouch;

g. a handle for holding and positioning said pouch, and operatively connecting with said pouch;

h. said handle comprising a band having a first band end extending beyond said first pouch end;

i. said band having a second band end extending beyond said second pouch end;

j. said band being of sufficient length with the band wrapped around the torso of a person so that the first band end and the second band end overlap for positioning said receptacle on said person;

k. said pouch being relatively long and relatively shallow in depth so that the long part of said pouch is many times the depth of said pouch;

l. a connecting means for joining said first band end and said second band end;

m. said connecting means comprising a first attaching means at said first band end and a second attaching means at said second band end;

n. with said first attaching means and said second attaching means in contact said first band end and said second band end are joined forming a continuous band encircling the torso of said person;

o. the long upper part of said rear pouch panel joining a front panel of said band to define a horizontal opening in said pouch for receiving said medical apparatus;

p. said pouch being of a pliable, flexible material which can be folded so that said material can overlap itself;

q. part of said medical apparatus being in said pouch;

r. said medical apparatus comprising a drain tube and a fluid collection bulb; and s. said drain tube operatively connecting with said fluid collection bulb and with a patient for allowing fluid to drain from said patient to said collection bulb.

4. A combination of a receptacle and medical apparatus and comprising:

a. a unitary one piece pouch comprising a front pouch panel and a rear pouch panel and having a first pouch end and a second pouch end;

b. said front pouch panel and said rear pouch panel joining at said first pouch end;

c. said front pouch panel and said rear pouch panel joining at said second pouch end;

d. the upper part of said front pouch panel folding back on itself and joining itself;

e. the upper part of said rear pouch panel folding back on itself and joining itself;

f. the upper part of said front pouch panel and the upper part of said rear pouch panel being separate and defining an opening;

g. said unitary one piece pouch defining a bottom;

h. said opening allowing the ingress and egress of said medical apparatus into said pouch and out of said pouch;

i. a handle for holding and positioning said pouch, and operatively connecting with said pouch;

j. said pouch being relatively short in length and relatively deep in depth so that the deep part is greater than said length;

k. said handle having a first end and a second end;

l. said first end operatively connecting with said pouch;

m. said first end connecting with the upper part of said pouch rear panel;

n. said second end connecting with the upper part of said pouch rear panel;

o. said first end and said second end being spaced apart;

p. part of said medical apparatus being in said pocket;

q. said medical apparatus comprising a fluid collection bulb in said receptacle and supported by said receptacle;

r. forming said receptacle to have a plurality of openings to allow an aqueous medium to escape from the receptacle; and s. selecting said receptacle to be hydrophobic.

5. A process for forming a receptacle for receiving and supporting medical apparatus, said process comprising:

a. forming a unitary one piece pouch comprising a front pouch panel and a rear pouch panel and having a first pouch end and a second pouch end;

b. joining said front pouch panel and said rear pouch panel at said first pouch end;

c. joining said front pouch panel and said rear pouch panel at said second pouch end;
d. the upper part of said front pouch panel and the upper part of said rear pouch panel being separate and defining an opening;
e. said unitary one piece pouch defining a bottom;
f. forming said opening to allow the ingress and egress of said medical apparatus into said pouch and out of said pouch;
g. forming a handle for holding and positioning said pouch, and operatively connecting with said pouch;
h. forming said handle to comprise a band having a first band end extending beyond said first pouch end;
i. forming said band to comprise a second band end extending beyond said second pouch end;
j. forming said band of sufficient length so that with the band wrapped around the torso of a person the first band end and the second band end overlap for positioning said receptacle on said person;
k. forming said pouch to be relatively long in length and relatively shallow in depth so that the long part of said pouch is many times the depth of said pouch;
l. joining said first band end and said second band end;
m. attaching a connecting means at said first band end and a connecting means at said second band end;
n. with said first attaching means and said second attaching means in contact said first band end and said second band end are joined forming a continuous band encircling the torso of said person;
o. joining the long upper part of said rear pouch panel to the front panel of said band to define a horizontal opening in said pouch for receiving said medical apparatus; and
p. forming said pouch being of a pliable, flexible material which can be folded so that the material can overlap itself.

6. A process for forming a receptacle for receiving and supporting medical apparatus, said process comprising:
a. a unitary one piece pouch comprising a front pouch panel and a rear pouch panel and having a first pouch end and a second pouch end;
b. said front pouch panel and said rear pouch panel joining at said first pouch end;
c. said front pouch panel and said rear pouch panel joining at said second pouch end;
d. folding the upper part of said front pouch panel back on itself and joining itself;
e. folding the upper part of said rear pouch panel back on itself and joining itself;
f. forming the upper part of said front pouch panel and the upper part of said rear pouch panel to be separate and to define an opening;
g. forming said unitary one piece pouch to have a bottom;
h. forming said opening to allow the ingress and egress of said medical apparatus into said pouch and out of said pouch;
i. forming a handle for holding and positioning said pouch, and operatively connecting with said pouch;
j. forming said pouch to be relatively short in length and relatively deep in depth so that said deep part is greater than said length;
k. forming said handle to have a first end and a second end;
l. operatively connecting said first end with said pouch;
m. operatively connecting said first end with the upper part of said pouch rear panel;
n. operatively connecting said second end with the upper part of said pouch rear panel;
o. spacing apart said first end and said second end;
p. selecting said receptacle to have a plurality of openings to allow an aqueous medium to escape from the receptacle; and
q. selecting said receptacle to be hydrophobic.

7. A process for making more comfortable a person having a drainage tube both inside of the person and outside of the person, said process comprising:
a. forming a unitary one piece pouch comprising a front pouch panel and a rear pouch panel and having a first pouch end and a second pouch end;
b. joining said front pouch panel and said rear pouch panel at said first pouch end;
c. joining said front pouch panel and said rear pouch panel at said second pouch end;
d. the upper part of said front pouch panel and the upper part of said rear pouch panel being separate and defining an opening;
e. said unitary one piece pouch defining a bottom;
f. forming said opening to allow the ingress and egress of said medical apparatus into said pouch and out of said pouch;
g. forming a handle for holding and positioning said pouch, and operatively connecting with said pouch;
h. forming said handle to comprise a band having a first band end extending beyond said first pouch end;
i. forming said band to comprise a second band end extending beyond said second pouch end;
j. forming said band of sufficient length so that with the band wrapped around the torso of a person the first band end and the second band end overlap for positioning said receptacle on said person;
k. forming said pouch to be relatively long in length and relatively shallow in depth so that the long part of said pouch is many times the depth of said pouch;
l. joining said first band end and said second band end;
m. attaching a connecting means at said first band end and a connecting means at said second band end;
n. with said first attaching means and said second attaching means in contact said first band end and said second band end are joined forming a continuous band encircling the torso of said person;
o. joining the long upper part of said rear pouch panel to the front panel of said band to define a horizontal opening in said pouch for receiving said medical apparatus;
p. forming said pouch to be of a pliable, flexible material which can be folded so that the material can overlap itself
q. positioning a first receptacle on the person;
r. connecting a collection bulb with the outer part of the drainage tube; and
s. positioning the outer part of said drainage tube and said collection bulb in said first receptacle with said first receptacle supporting said drainage tube and said collection bulb.

8. A process for making more comfortable a person having a drainage tube both inside of the person and outside of the person, said process comprising:

a. a unitary one piece pouch comprising a front pouch panel and a rear pouch panel and having a first pouch end and a second pouch end;

b. said front pouch panel and said rear pouch panel joining at said first pouch end;

c. said front pouch panel and said rear pouch panel joining at said second pouch end;

d. folding the upper part of said front pouch panel back on itself and joining itself;

e. folding the upper part of said rear pouch panel back on itself and joining itself;

f. forming the upper part of said front pouch panel and the upper part of said rear pouch panel to be separate and to define an opening;

g. forming said unitary one piece pouch to define a bottom;

h. said opening allowing the ingress and egress of a drainage to be into said pouch and out of said pouch;

i. forming a handle for holding and positioning said pouch, and operatively connecting with said pouch;

j. forming said pouch to be relatively short in length and relatively deep in depth so that said deep part is greater than said length;

k. forming said handle to have a first end and a second end;

l. operatively connecting said first end with said pouch;

m. operatively connecting said first end with the upper part of said pouch rear panel;

n. operatively connecting said second end with the upper part of said pouch rear panel;

o. spacing apart said first end and said second end;

p. selecting said receptacle to have a plurality of openings to allow an aqueous medium to escape from the receptacle;

q. selecting said receptacle to be hydrophobic;

r. positioning said first receptacle on the person;

s. connecting a collection bulb with the outer part of the drainage tube; and t. positioning the outer part of said drainage tube and said collection bulb in said first receptacle with said first receptacle supporting said drainage tube and said collection bulb.

9. A process for making a person more comfortable in taking a shower:

a. a unitary one piece pouch comprising a front pouch panel and a rear pouch panel and having a first pouch end and a second pouch end;

b. said front pouch panel and said rear pouch panel joining at said first pouch end;

c. said front pouch panel and said rear pouch panel joining at said second pouch end;

d. folding the upper part of said front pouch panel back on itself and joining itself;

e. folding the upper part of said rear pouch panel back on itself and joining itself;

f. forming the upper part of said front pouch panel and the upper part of said rear pouch panel to be separate and to define an opening;

g. forming said unitary one piece pouch to define a bottom;

h. forming said opening to allow the ingress and egress of said medical apparatus into said pouch and out of said pouch;

i. forming a handle for holding and positioning said pouch, and operatively connecting with said pouch;

j. forming said pouch to be relatively short in length and relatively deep in depth so that said deep part is greater than said length;

k. forming said handle to have a first end and a second end;

l. operatively connecting said first end with said pouch;

m. operatively connecting said first end with the upper part of said pouch rear panel;

n. operatively connecting said second end with the upper part of said pouch rear panel;

o. spacing apart said first end and said second end;

p. selecting said receptacle to have a plurality of openings to allow an aqueous medium to escape from the receptacle;

q. selecting said receptacle to be hydrophobic;

r. positioning a first receptacle on the person;

s. connecting a collection bulb with the outer part of a drainage tube;

t. positioning the outer part of said drainage tube and said collection bulb in said first receptacle with said first receptacle supporting said drainage tube and said collection bulb;

u. a support external to the person; and v. positioning said receptacle and said bulb on said support external to said person to allow freedom of movement by the person taking the shower.

* * * * *